(12) United States Patent
Nauber et al.

(10) Patent No.: US 7,608,177 B2
(45) Date of Patent: Oct. 27, 2009

(54) ELECTROCHEMICAL GAS SENSOR

(75) Inventors: Andreas Nauber, Lübeck (DE); Dieter Krüger, Stockelsdorf (DE); Michael Sick, Timmendorfer Strand (DE); Christoph Bernstein, Lübeck (DE); Michael Dietrich, Stockelsdorf (DE); Hans-Jürgen Busack, Lübeck (DE); Rigobert Chrzan, Bad Oldesloe (DE); Kathrin Hermann, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 763 days.

(21) Appl. No.: 11/232,562

(22) Filed: Sep. 22, 2005

(65) Prior Publication Data

US 2006/0124458 A1   Jun. 15, 2006

(30) Foreign Application Priority Data

Dec. 9, 2004   (DE) .................. 10 2004 059 280

(51) Int. Cl.
*C25B 3/00*   (2006.01)
*C25B 1/10*   (2006.01)
*C25B 1/24*   (2006.01)
*C25B 1/00*   (2006.01)

(52) U.S. Cl. .................. 204/424; 204/411; 204/412; 204/418; 204/419

(58) Field of Classification Search .................. 204/411, 204/412, 415, 418–419, 424, 403, 406
See application file for complete search history.

(56) References Cited

U.S. PATENT DOCUMENTS

| | | | |
|---|---|---|---|
| 4,308,751 A * | 1/1982 | Thurner et al. ................. | 73/627 |
| 4,406,770 A * | 9/1983 | Chan et al. .................. | 204/406 |
| 5,298,146 A * | 3/1994 | Braden et al. ................ | 204/406 |
| 5,830,337 A * | 11/1998 | Xu ............................... | 204/400 |
| 5,932,079 A * | 8/1999 | Haupt et al. ................. | 204/415 |
| 6,080,294 A * | 6/2000 | Shen et al. ................... | 204/415 |
| 7,034,943 B1 * | 4/2006 | Moeckli et al. ............. | 356/423 |
| 2002/0070128 A1 * | 6/2002 | Beckmann .................. | 205/775 |

(Continued)

FOREIGN PATENT DOCUMENTS

DE   197 26 453   1/1999

(Continued)

*Primary Examiner*—Brian J. Sines
*Assistant Examiner*—Gurpreet Kaur
(74) *Attorney, Agent, or Firm*—McGlew and Tuttle, P.C.

(57) ABSTRACT

An electrochemical gas sensor with a stacked arrangement of electrodes and nonwoven layers arranged in parallel, comprising at least one measuring electrode (3) and at least one counterelectrode (5). A porous membrane (8) that is permeable to air is in contact with the stacked arrangement of electrodes and nonwoven layers arranged in parallel at least on one side, at least one layer of a hydrophilic nonwoven (7) is located between the electrodes. The porous membrane (8) that is permeable to air and the hydrophilic nonwoven (7) extend into a separate equalization volume (9), which is filled with electrolyte at least partially and is located at least partially in one plane with the electrodes. The separate equalization volume (9) surrounds the electrode arrangement at least partially in this plane, and the porous membrane (8) that is permeable to air is exposed to ambient pressure at least in partial areas. Such sensors are characterized by a flat shape, high insensitivity to shocks, independence from the position, and high tolerance to variations in environmental humidity.

27 Claims, 5 Drawing Sheets

U.S. PATENT DOCUMENTS

| | | | |
|---|---|---|---|
| 2003/0019747 A1* | 1/2003 | Saffell et al. | 204/400 |
| 2003/0046980 A1* | 3/2003 | Kiesele et al. | 73/31.05 |
| 2004/0128823 A1* | 7/2004 | Mole | 29/592.1 |
| 2007/0181423 A1* | 8/2007 | Collins | 204/400 |

FOREIGN PATENT DOCUMENTS

| | | |
|---|---|---|
| EP | 1 179 731 A2 | 2/2002 |
| GB | 2 292 804 | 3/1996 |
| GB | 2 371 873 | 8/2002 |
| GB | 2 421 577 | 6/2006 |
| JP | 2004361282 | 12/2004 |

* cited by examiner

ELECTROCHEMICAL GAS SENSOR

CROSS REFERENCE TO RELATED APPLICATIONS

This application claims the benefit of priority under 35 U.S.C. § 119 of German Application DE 10 2004 059 280.2 filed Dec. 9, 2004, the entire contents of which are incorporated herein by reference.

FIELD OF THE INVENTION

The present invention pertains to an electrochemical gas sensor with a stacked arrangement of electrodes and nonwoven (nonwoven material) layers arranged in parallel.

BACKGROUND OF THE INVENTION

Electrochemical gas sensors are used in many different ways in the analytical qualitative and quantitative measurement of gases. Conversion of the analyte, which can be used for making qualitative and quantitative statements because of its selectivity and its accessibility on the basis of unambiguously measurable electric variables, takes place at a measuring electrode, which reacts selectively with the gas to be detected.

In a minimal configuration, an electrochemical gas sensor has a measuring electrode and a counterelectrode. In an expanded version, which is often called a three-electrode sensor, a reference electrode is added to this configuration. The electrodes are often completely surrounded by an electrolyte, the electrolyte or the space accommodating it in the sensor housing essentially determining the overall size of the electrochemical sensor. In the effort to achieve a reduction of the size of the device, various variants have become known, in which stacked arrangements of electrodes and nonwoven layers are used, the electrodes communicating via electrolyte volumes enclosed in the nonwoven layers. To achieve sufficient service lives and insensitivity to variations in the environmental humidity level, separate electrolyte volumes are used, as a rule, in such sensors, and the individual nonwoven layers are in contact with these separate electrolyte volumes via absorbent connections. The electrode-nonwoven stacks are usually arranged behind electrolyte chambers acting as a storage volume, and the resulting overall height of such gas sensors is therefore determined by the height of these electrolyte chambers and the thickness of the stacked arrangement.

To obtain reliable and reproducible measured values during the use of electrochemical gas sensors, a number of boundary conditions are to be taken into consideration. These include the ability of the sensor to release the pressure in its interior by an effective pressure equalization with the environment and to avoid undesired creep processes of the electrolyte as much as possible.

Another important boundary condition is the continuous and constant wetting of the active electrode areas with electrolyte, because considerable distortions of the measured signal may otherwise occur. General requirements on an electrochemical gas sensor are, furthermore, a relative insensitivity to shocks and impacts, low position sensitivity as well as general technological requirements such as the possibility of manufacture at a low cost and simple applicability.

SUMMARY OF THE INVENTION

The object of the present invention is to provide an electrochemical gas sensor that satisfies the above-mentioned requirements in an optimal manner.

According to the present invention an electrochemical gas sensor is provided comprising a stacked arrangement of electrodes and nonwoven layers arranged in parallel, comprising at least one measuring electrode and at least one counterelectrode, wherein a preferably porous membrane, which is permeable to air and is electrolyte-proof (impermeable to the electrolyte), is in contact with the stacked arrangement of electrodes and nonwoven layers arranged in parallel at least on one side. At least one layer of a hydrophilic nonwoven, for example, a glass nonwoven, is arranged between the electrodes. The porous membrane that is permeable to air and the hydrophilic nonwoven extend into a separate equalization volume, which is filled at least partially with electrolyte and which is located at least partially in one plane with the electrodes, surrounding the electrode arrangement at least partially in this plane. The porous membrane that is permeable to air is exposed to ambient pressure at least in partial areas. Due to such a design of a gas sensor, it is achieved that the overall height is further reduced by the electrodes with the electrolyte volume being located at least partially in one plane, as a result of which the addition of the overall height of the two components is avoided.

Due to the special embodiment of the electrolyte volume in the form of a circular cavity, which is partially filled with electrolyte, a high degree of position independence of the electrochemical gas sensor is achieved. Due to the fact that an air-permeable membrane partially extends into the electrolyte volume or the cavity intended to accommodate it, but is, on the other hand, partially exposed to ambient pressure, effective pressure equalization takes place with the environment via the porous structure of this air-permeable membrane, as a result of which an excessive increase and an excessive reduction of the internal pressure in the electrolyte volume is avoided.

The hydrophilic nonwoven between the electrodes ensures sufficient wetting, which is always guaranteed, because the hydrophilic nonwoven extends at least partially into the electrolyte-filled equalization volume. If more than two electrodes are used, it is guaranteed that each electrode is at least in contact with a hydrophilic nonwoven. A hydrophilic nonwoven designed according to the present invention is arranged in this case at a plurality of points in the stacked arrangement comprising electrodes and nonwoven layers arranged in parallel. Nevertheless, mostly only a hydrophilic nonwoven will be referred to below. The use of nonwoven as an electrolyte carrier brings about good insensitivity to vibrations.

It is especially advantageous technologically if the counterelectrode is applied to the porous, air-permeable membrane. The membrane is used in this case at the same time as a means for pressure equalization and as a counterelectrode carrier. An especially high level of position insensitivity of the sensor according to the present invention is achieved if the equalization volume surrounds the electrode arrangement along a closed figure. In an advantageous embodiment, the porous, air-permeable membrane, which is in contact with the counterelectrode, consists of PTFE. In connection with the volume for accommodating the electrolyte, which volume surrounds the electrode arrangement at least partially, an especially advantageous embodiment can be obtained if the hydrophilic nonwoven and the porous, air-permeable membrane occupy a central area, for example, in the form of a circular surface, the porous, air-permeable membrane having strips that are arranged in a star-shaped pattern (i.e., with portion extending radially outwardly from a central region) and extend from the edge of the central area into the equalization volume. Thus, in case of an at least partial filling of the electrolyte volume, it is thus guaranteed, nearly independently from the position, that at least some of the strips arranged in a star-shaped pattern extend into an air bubble located in the equalization volume rather than into the electrolyte and can thus ensure an effective pressure equalization with the environment.

It is especially advantageous if the hydrophilic nonwoven likewise has strips arranged in a star-shaped pattern, which start from the edge of such a central area and extend into the equalization volume, the end of at least one of these strips immersing into the electrolyte in the equalization volume. This requirement can likewise be advantageously met with the embodiment of the electrolyte volume according to the present invention, doing so independently from the position of the electrochemical sensor. It is advantageous for the high reliability of operation of the electrochemical sensor if the hydrophilic nonwoven and the porous, air-permeable membrane have at least three strips arranged in a star-shaped pattern, which extend from the edge of a circular surface into the equalization volume. It is especially advantageous if the hydrophilic nonwoven and the porous, air-permeable membrane have four strips arranged in a star-shaped pattern, which extend from the edge of the circular surface intro the equalization volume. It is thus ensured that nearly independently from the direction of the sensor and nearly independently from the degree of filling of the electrolyte volume, at least one of the strips of the air-permeable membrane that are arranged in a star-shaped pattern is always in contact with an air bubble and at least one of the strips of the hydrophilic nonwoven that are arranged in a star-shaped pattern is in contact with the electrolyte, which guarantees the ability of the sensor according to the present invention to function under all circumstances.

To prevent the undesired entry of gas into the electrolyte through the porous, air-permeable membrane, it is advantageous if a filter is contained, by which the gases that reach the porous, air-permeable membrane from the atmosphere surrounding the sensor are filtered. This filter may contain, for example, absorber substances, which nearly rule out the penetration of undesired gases.

To additionally protect the filter on the atmospheric side, it is, furthermore, advantageous to provide a cover, through which leads an opening that determines the entry of gas. Sufficient pressure equalization is thus ensured and rapid saturation of the filter is nevertheless avoided. This cover of the filter may advantageously be a name plate, which carries a label characterizing the sensor.

In a sensor configuration that can advantageously be used for more accurate gas measurements, a reference electrode is integrated, namely, in such a way that the electrode arrangement contains at least one reference electrode, which is embedded between the measuring electrode and the counterelectrode in a hydrophilic nonwoven on both sides and has an area that is smaller than the area of the measuring electrode and smaller than the area of the counterelectrode. As a result, diffusion processes taking place between the measuring electrode and the counterelectrode are not interfered with in such a way that the electrochemical reactions or current flows necessary for the measurement purposes would be prevented from taking place.

It is especially advantageous if a diffusion-inhibiting membrane is arranged between the measuring electrode and the counterelectrode. This prevents substances that may be formed at the counterelectrode or can penetrate into the sensor in the vicinity of the counterelectrode from distorting the measuring result due to diffusion in the direction of the measuring electrode. This becomes especially significant when an electrochemical detection reaction is organized such that an analyte decomposes or is converted at the measuring electrode, whereas it is formed anew at the counterelectrode, as it happens in some types of oxygen sensors. However, the ion diffusion through the electrolyte must not be interrupted, and such a diffusion-inhibiting membrane may therefore either cover only part of the sensor cross section or be designed, in an advantageous embodiment, as a diffusion-inhibiting membrane having a weaker barrier action for ions than for neutral species. Such membranes are already known under the term Nafion from other applications. A nonselective diffusion-inhibiting membrane advantageously covers 50-95% of the cross section of the sensor and has an oxygen permeability that is lower than $5*10^{-16}$ kg m*m$^{-2}$ sec$^{-1}$ Pa$^{-1}$ and preferably $1*10^{-16}$ m*m$^{-2}$ sec$^{-1}$ Pa$^{-1}$.

A sensor according to the present invention can be manufactured in a simple manner if the sensor is surrounded by a two-part housing, whose parts are connected with one another by a snap connection, the parts of the housing being shaped such that the arrangement comprising parallel electrodes, nonwoven and a membrane that is permeable to air is fixed in a nonpositive manner. Due to forces generated during the fixing, there will, moreover, be good contact between electrolyte-carrying nonwoven structures and electrodes, as a result of which an increase in the reliability of operation of the sensor is brought about.

To avoid the escape of the electrolyte from the storage volume even in case of multipart sensor housings, it is advantageous if the contact area between the housing parts has an electrolyte-proof sealing. The reference electrode advantageously consists of a sintered mixture of a metal and its metal oxide, preferably from the platinum group, the iridium group or gold.

In an alternative advantageous embodiment, the reference electrode consists of doped diamond or diamond-like carbon, as a result of which a high degree of independence from variations in the pH value or the pO$_2$ value in the electrolyte is achieved.

It is advantageous, furthermore, if the sensor comprises readable means for storing sensor-specific data. These readable means for storing sensor-specific data may comprise, for example, an EEPROM or a transponder and be designed such that storage of type information and/or information on the sensitivity of the sensor can be performed on the basis of a performed gauging, calibration and/or other information relevant for approval.

It is especially advantageous if the measuring electrode comprises a plurality of sectors made of different electrode materials, which are electrically separated from one another. Due to the selectivity of the electrochemical reaction, which is usually suitable for the detection of an analyte, it is thus possible to simultaneously perform the detection of a plurality of gases to be determined.

To secure the sensor against pressure variations that may occur in the environment, it may be advantageous if the sensor housing has a gas inlet opening for the entry of the gas to be measured, which communicates with the environment of the sensor via a pneumatic damping element. Pressure variations, which could lead to damage to the sensor or to a temporary distortion of the measured signal, are thus prevented from occurring.

The electrodes and/or the readable means for storing sensor-specific data are advantageously contacted in a sensor according to the present invention via contact pins, which can be inserted into the sensor housing and which are in firm contact in the inserted state with conductive connection means, which lead to the electrodes and/or the readable means for storing sensor-specific data and are electrically connected with same. These connection means may advantageously comprise wires, which lead at least partially through areas provided with liquid seals. Electrolyte is thus effectively prevented from escaping along the wires.

Sensors according to the present invention can be adapted to different measurement requirements without problems by selecting a suitable combination of electrolyte and electrode material, without any special design measures becoming necessary on the housing.

The present invention will be explained in greater detail on the basis of exemplary embodiments. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
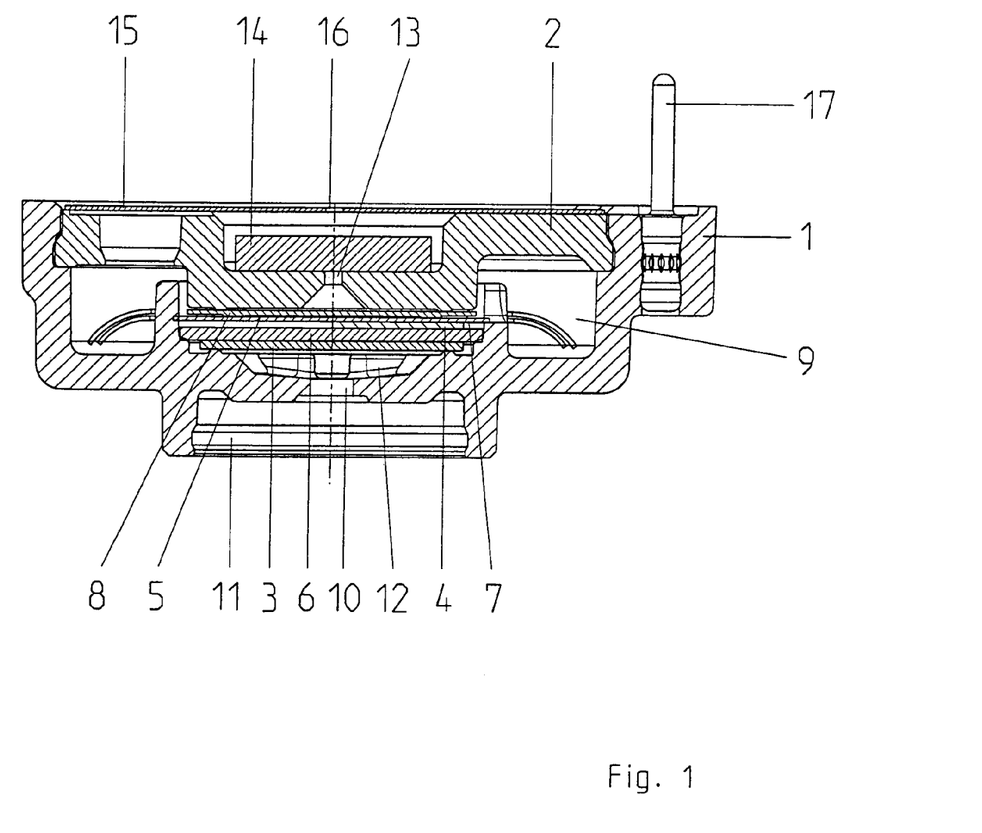
FIG. 1 is a sectional view of an electrochemical sensor according to the present invention.

Referring to the drawings in particular, FIG. 1 shows a sectional view of an electrochemical sensor according to the present invention, which is designed as a three-electrode sensor, in the horizontal orientation. The sensor comprises a two-part housing, which comprises a front housing part 1 and a rear housing part 2. The housing is made of an elastically deformable plastic material. Both housing parts 1, 2 have an edge shape by which they can be connected in a positive-locking manner in the manner of a snap connection. The connected housing parts fix in the central area of the sensor a stacked arrangement of electrodes and nonwoven layers arranged in parallel, the individual components of the stacked arrangement being pressed against each other in a functionally advantageous manner. The stacked arrangement of electrodes and nonwoven layers arranged in parallel comprises a measuring electrode 3, a reference electrode 4, a counterelectrode 5, a hydrophilic nonwoven layer 6 between the measuring electrode 3 and the reference electrode 4, a hydrophilic nonwoven layer 7 between the reference electrode 4 and the counterelectrode 5, and a porous membrane 8 made of PTFE, which is permeable to air and is located between the counterelectrode 5 and the rear housing part 2. The porous membrane 8 that is permeable to air and the counterelectrode 5 are connected to one another such that the counterelectrode 5 forms an elevated area on the porous membrane 8 that is permeable to air, which elevated area is in firm contact with the hydrophilic nonwoven layer 7. The stacked arrangement comprising electrodes and nonwoven layers arranged in parallel is surrounded by an equalization volume 9, which is partially filled with electrolyte. Due to the special design of the front housing part 1, the stacked arrangement comprising electrodes and nonwoven layers arranged in parallel and the partially electrolyte-filled equalization volume 9 are extensively separated from one another. Only extensions of the hydrophilic nonwoven layer 7 and of the porous membrane 8 that is permeable to air extend into the partially electrolyte-filled equalization volume 9 through openings in the separating housing part. A gas inlet opening 10 leads through the front housing part 1 up to the measuring electrode 3. The front housing part 1 has a holding structure, which is provided with a circumferential groove 11 and which makes it possible to arrange different adapters in front of the gas inlet opening. Such adapters may have, for example, openings limiting the entry of gas and are thus used to adapt the sensor to greatly different analyte concentrations. The measuring electrode 3 is supported by a web arrangement 12 integrated in the front housing part. It is guaranteed as a result that gas entering through the gas inlet opening 10 can come into contact with the measuring electrode 3 over its entire area. The rear housing part 2 has in the middle a pressure equalizing opening 13, via which the porous membrane 8 that is permeable to air is in contact with the environment of the sensor. A filter 14 is located on the side of the environment in front of the pressure equalizing opening 13. The rear housing part is closed off on the outside by the name plate 15, which has a central hole 16. The small diameter of this hole offers, on the one hand, the possibility of sufficient pressure equalization with the environment of the sensor, but, on the other hand, it prevents the exchange of gas with the environment in such a way that it leads to an effective prolongation of the service life of the filter 14.

There is a uniform electrolyte filling level in the entire equalization volume 9 in the horizontal position of the sensor. The ability of the sensor to function is guaranteed when parts of the hydrophilic nonwoven layer 7 extend into the electrolyte and parts of the porous membrane 8 that is permeable to air are located in air-filled areas of the equalization volume 9. If the direction of the sensor changes, a higher electrolyte level will become established in some areas of the equalization volume 9, and the electrolyte can flow off from other areas. However, at least one strip-shaped extension will always extend into the electrolyte and another one will end in an air-filled area of the equalization volume 9 due to the star-shaped arrangement of strip-shaped extensions of the hydrophilic nonwoven 7 and of the porous membrane 8 that is permeable to air. As a result, an effective pressure equalization with the environment and constant impregnation of the nonwoven layers is achieved independently from the position of the sensor. As a result, the electrodes are always wetted even under dry ambient conditions. The reference electrode 4 has a markedly smaller area than the other electrodes in this example. As a result, the hydrophilic nonwoven layers 6, 7 can touch each other in sufficiently large surface areas to guarantee an effective exchange of electrolyte. It is sufficient for the mode of action of the sensor according to the present invention in this case if one of the hydrophilic nonwoven layers 6, 7, the nonwoven layer 7 between the counterelectrode 5 and the reference electrode 4 in this case, has extensions that extend into the electrolyte. However, a plurality of nonwoven layers, which have such extensions, may also be used as an alternative.

Recesses, in which contact pins 17 provided for connecting the sensor to corresponding adapters can be fastened in a non-positive manner, are located in the edge area of the front housing part.

Figure 2:
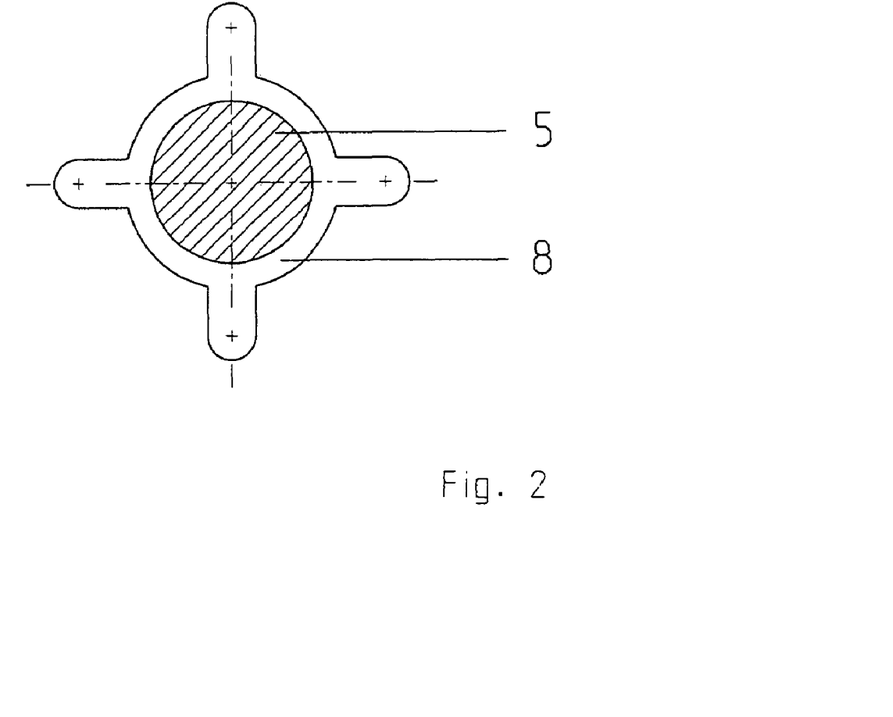
FIG. 2 is a corresponding counterelectrode, which is located on a porous membrane that is permeable to air.

FIG. 2 shows a counterelectrode 5 according to the present invention, which is located on a porous membrane 8 that is permeable to air. The porous membrane 8 that is permeable to air comprises essentially a circular central area, from the edge of which four strips arranged in a star-shaped pattern originate, which extend from the edge of the central area into the equalization volume in the completely mounted sensor.

Figure 3:
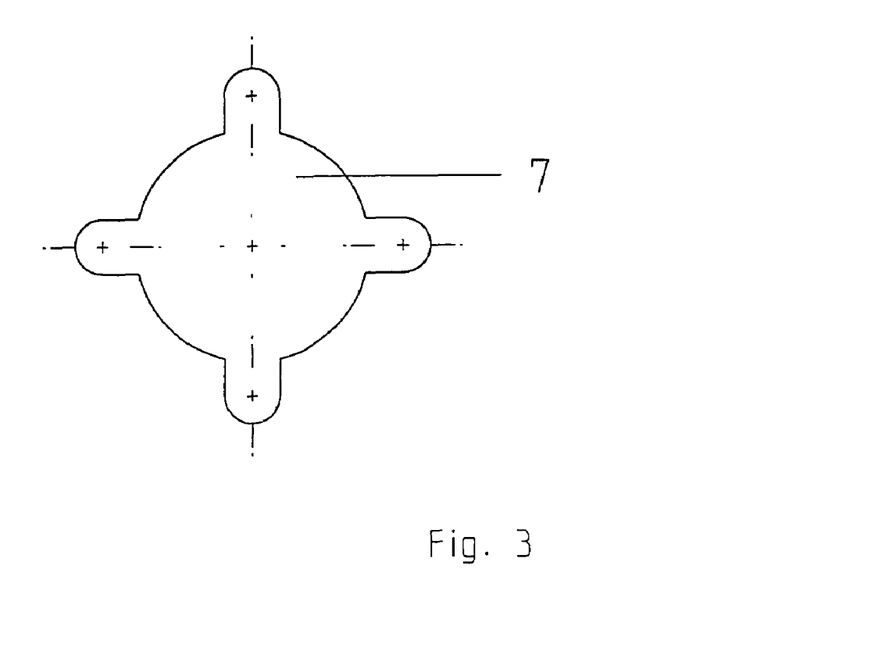
FIG. 3 is the shape of a hydrophilic nonwoven designed advantageously, as it can be used between individual electrodes.

FIG. 3 shows a layer of a hydrophilic nonwoven 7, which is designed according to the present invention and likewise comprises a circular central area, from the edge of which four strips originate, which are arranged in a star-shaped pattern, extend from the edge of the central area into the compensating volume in the completely mounted state of the sensor and ensure uniform impregnation of the nonwoven 7 due to contact with the electrolyte.

Figure 4:
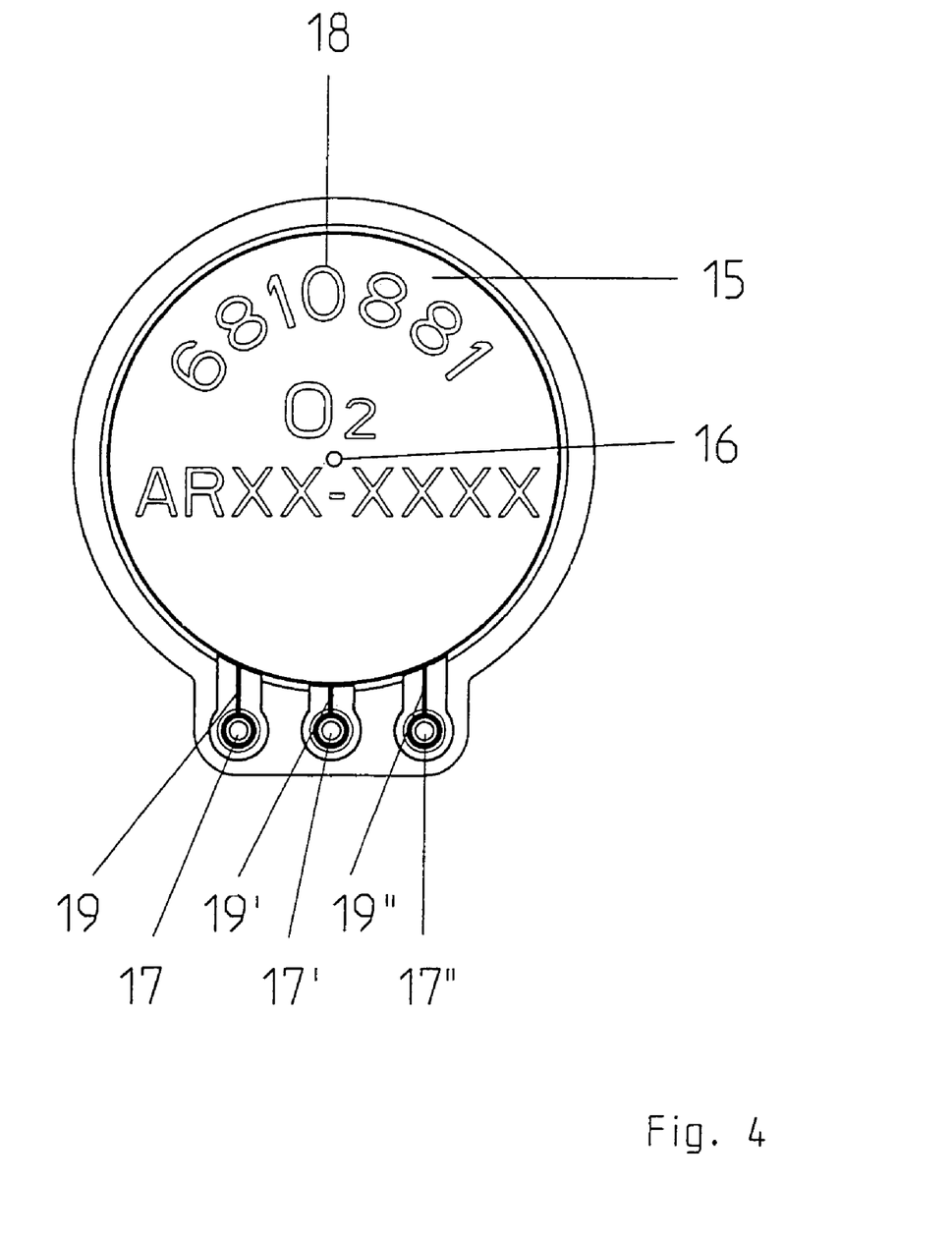
FIG. 4 is a view of the rear side of a sensor according to the present invention with a cover designed as a name plate.

FIG. 4 shows a view of the rear side of a sensor according to the present invention with a cover designed as a name plate 15. The name plate 15 has a central hole 16 limiting the entry of gas and is provided with an engraving 18 characterizing the sensor. Contact wires 19, 19', 19" lead from the electrodes (not visible) to contact pins 17, 17', 17", which are inserted into the edge area of the front housing part 1.

Figure 5:
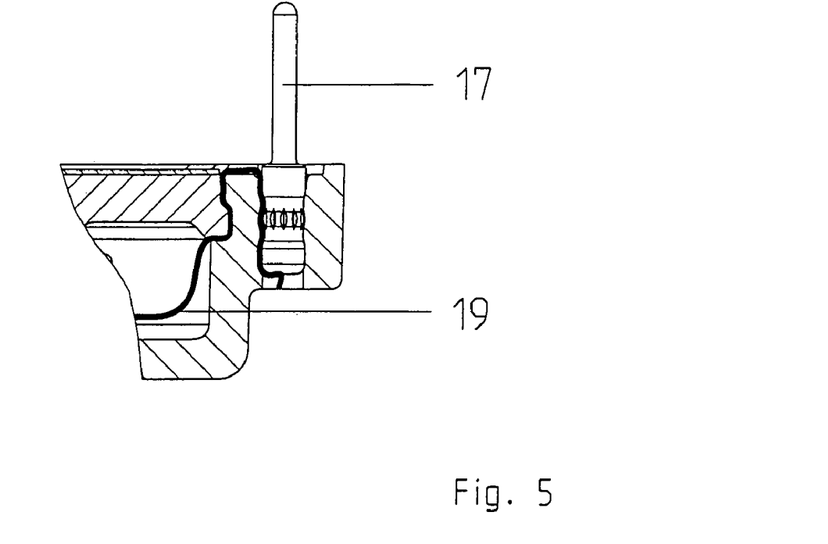
FIG. 5 is the area of the sensor housing, into which individual contact pins can be inserted.

FIG. 5 shows the edge area of the sensor housing, into which individual contact pins 17 can be inserted. The electrodes are contacted via thin metal wires 19. These preferably consist of Pt, Pd, Au or Ta. These wires 19 are not soldered to the contact pins 17, but are clamped between the contact pins 17 and the housing wall when the contact pins 17 are inserted. This makes possible a simple, rapid and reliable manufacture. There is no risk that cold soldering joints would be formed. In addition, the risk of high thermal load on the sensor during manufacture is eliminated. The wires 19 are led in this example through the connection area between the two housing parts. A liquid seal can be used now to seal the passage.

Figure 6:
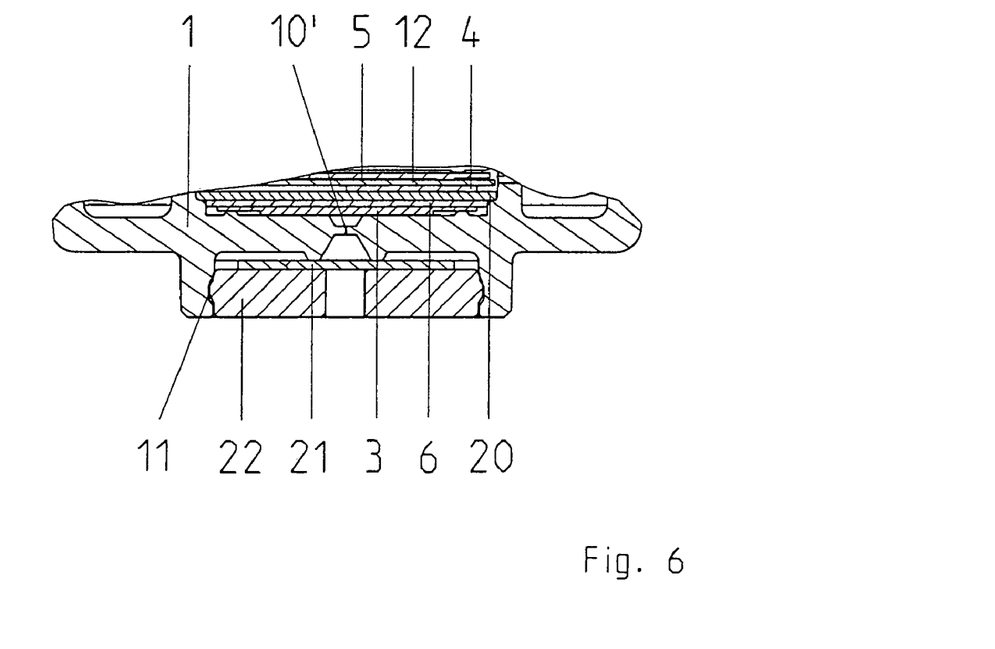
FIG. 6 is a detail of a sensor according to the present invention in an embodiment as an oxygen sensor with a pneumatic damping element.

FIG. 6 shows a detail of a sensor according to the present invention in an embodiment as an oxygen sensor with a pneumatic damping element. The oxygen sensor operates according to a principle according to which oxygen is formed at the counterelectrode 5. Due to the electrodes being arranged at closely spaced locations, there is a risk that this oxygen reaches the measuring electrode and leads to a distortion of the measured signal there. An ion-conducting membrane (Nafion), which prevents the diffusion of oxygen but hardly compromises the ion transport, is therefore located as a diffusion-inhibiting membrane 20 between the hydrophilic nonwoven layer 6 behind the measuring electrode 3 and the reference electrode 4 in this embodiment. A further adaptation to operation as an oxygen sensor is represented by the design of the gas inlet opening 10' as a narrow capillary. Since sensors in which the inlet of gas is limited via capillaries are sensitive to pressure shocks, a pneumatic damping element is arranged upstream of the capillary. This damping element comprises a porous PTFE membrane 21, which is fixed by a holding element 22, which is fastened in the circumferential groove 11 of the front housing part 1.

Figure 7:
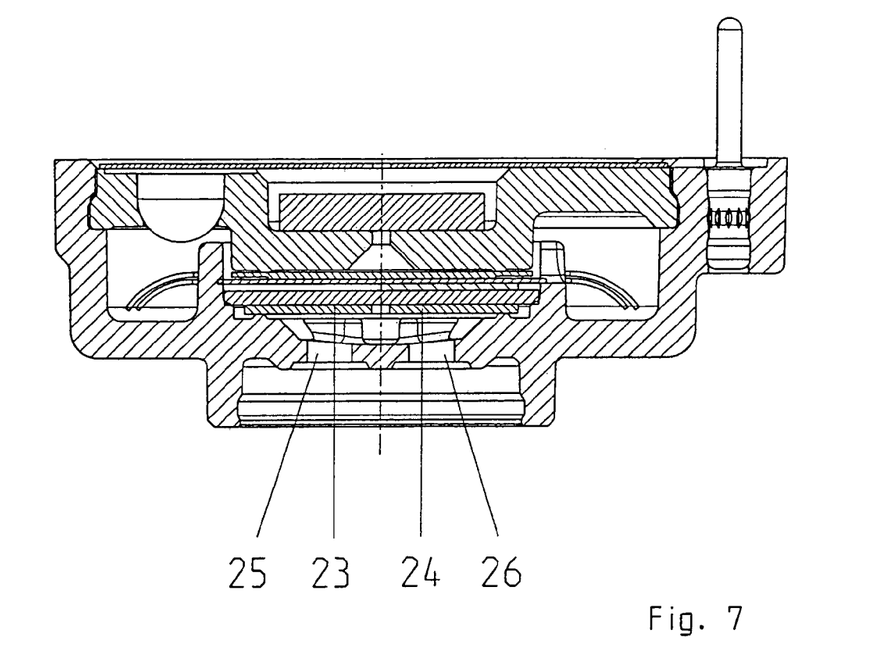
FIG. 7 is a sectional view of an electrochemical sensor according to the present invention in an embodiment with a measuring electrode divided into two sectors.

FIG. 7 shows a sectional view of an electrochemical sensor according to the present invention in an embodiment with a measuring electrode divided into two sectors 23, 24. The design extensively resembles the design according to FIG. 1. However, separate gas inlet openings 25, 26 are present, corresponding to the sectors 23, 24 acting as measuring electrodes, in order to lead the gas to be measured as effectively as possible to the individual sectors 23, 24. Due to the selection of the combination of electrolyte and electrode material and the inherent selectivity of these combinations, sensors according to the present invention can be used for the selective measurement of different gases. Typical representatives of such gases to be detected are $CO$, $H_2S$, $O_2$, $SO_2$, $NO_2$, $NH_3$, $HCN$, $Cl_2$, $HCl$, $HF$, $CO_2$, $PH_3$, $NO$, etc. If different electrode materials are used for the individual sectors 23, 24 of the measuring electrode, different gases can be measured simultaneously with a sensor with divided measuring electrode if the necessary electrochemical reactions require the same electrolyte. If necessary, different bias voltages may be applied to the individual sectors 23, 24 of the measuring electrode. It is also possible to admit gas to the individual sectors 23, 24 via completely uncoupled areas. The geometric conditions in front of the individual sectors can thus be adapted to different measured gas concentrations, which markedly expands the range of applications of sensors according to the present invention for the analysis of different gas mixtures.

Figure 8:
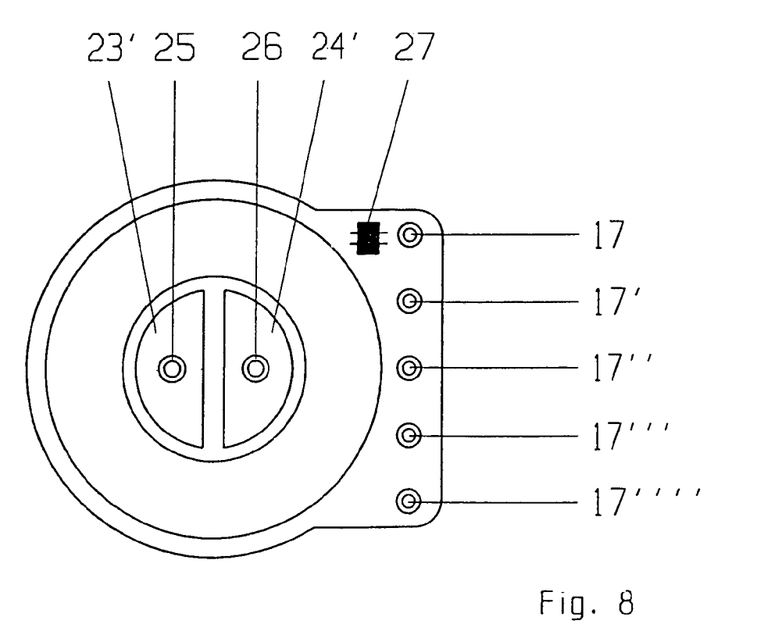
FIG. 8 is a simplified top view of a sensor according to the present invention with five contact pins and a two-part measuring electrode.

FIG. 8 shows a simplified top view of a sensor according to the present invention with five contact pins and a two-part measuring electrode. Two half moon-shaped electrode sectors 23', 24' are embedded in a transparent sensor housing. Two separate gas inlet openings 25, 26 lead to these sectors. There are five contact pins in the edge area of the sensor housing, the number of contact pins being able to be varied by simple technological measures. If the number of contact pins exceeds the number of electrodes or electrode sectors to be contacted, readable means 27 for storing sensor-specific data, which are embedded in the sensor housing, can be contacted via the extra contact pins.

While specific embodiments of the invention have been shown and described in detail to illustrate the application of the principles of the invention, it will be understood that the invention may be embodied otherwise without departing from such principles.

What is claimed is:

1. An electro chemical gas sensor, comprising:
   at least one measuring electrode;
   at least one counterelectrode;
   a nonwoven layer, said at least one measuring electrode and said at least one counterelectrode cooperating with said nonwoven layer to form a stacked arrangement of electrodes and said nonwoven layer arranged in parallel with said nonwoven layer being a hydrophilic nonwoven material layer arranged between said electrodes;
   a porous membrane, that is permeable to air, in contact on at least one side with said stacked arrangement of said electrodes and nonwoven layer arranged in parallel;
   a housing defining a stacked arrangement of electrodes volume with said stacked arrangement of electrodes therein and a separate equalization volume filled with electrolyte at least partially, said porous membrane that is permeable to air and said hydrophilic nonwoven material layer extending from said stacked arrangement of electrodes volume into said separate equalization volume filled with electrolyte at least partially, said separate equalization volume being located at least partially in a plane with said electrodes and circumferentially surrounding said stacked arrangement of electrodes at least partially in the plane, said porous membrane that is permeable to air being exposed to ambient pressure at least in partial areas.

2. A sensor in accordance with claim 1, wherein said counterelectrode is applied to said porous membrane that is permeable to air.

3. A sensor in accordance with claim 1, wherein said equalization volume surrounds the electrode arrangement along a closed figure.

4. A sensor in accordance with claim 1, wherein said porous membrane that is permeable to air consists of PTFE.

5. A sensor in accordance with claim 1, wherein said electrodes, said hydrophilic nonwoven and said porous membrane that is permeable to air occupy each essentially a circular area, wherein said porous membrane that is permeable to air has strips, which are arranged in a star-shaped pattern and extend from the edge of the circular area into said equalization volume.

6. A sensor in accordance with claim 5, wherein said hydrophilic nonwoven has strips which are arranged in a star-shaped pattern and extend from the edge of the circular area into said equalization volume, wherein the end of at least one of said strips is immersed into the electrolyte in said equalization volume.

7. A sensor in accordance with claim 1, wherein said hydrophilic nonwoven and said porous membrane that is permeable to air have at least three strips each that are arranged in a star-shaped pattern and extend from the edge of the circular area into said equalization volume.

8. A sensor in accordance with claim 7, wherein said hydrophilic nonwoven and said porous membrane that is permeable to air have said strips each that are arranged in a star-shaped pattern and extend from the edge of the circular area into said equalization volume.

9. A sensor in accordance with claim 1, further comprising a filter filtering gases that reach said porous membrane that is permeable to air from the atmosphere surrounding the sensor.

10. A sensor in accordance with claim 9, wherein said filter is protected on a side exposed of the atmosphere by a cover, through which leads an opening that determines the inlet of gas.

11. A sensor in accordance with claim 10, wherein said cover is a name or indicia plate with a label characterizing the sensor.

12. A sensor in accordance with claim 1, wherein said electrode arrangement contains at least one reference electrode embedded between said measuring electrode and said counterelectrode and embedded in said hydrophilic nonwoven on both sides and has an area that is smaller than the area of said measuring electrode and smaller than the area of said counterelectrode.

13. A sensor in accordance with claim 1, further comprising a diffusion-inhibiting membrane arranged between said measuring electrode and said counterelectrode.

14. A sensor in accordance with claim 13, wherein said diffusion-inhibiting membrane has a weaker barrier action against ions than against neutral species.

15. A sensor in accordance with claim 1, wherein said stacked arrangement of electrodes and nonwoven layer and said air-permeable membrane is surrounded by a two-part housing, with said two parts connected to one another by a snap connection, said two parts being shaped such that said stacked arrangement of electrodes and nonwoven layer and said air-permeable membrane is fixed in a non-positive manner.

16. A sensor in accordance with claim 15, wherein the contact area between said housing parts has an electrolyte-proof liquid seal.

17. A sensor in accordance with claim 12, wherein said stacked arrangement of electrodes includes a reference electrode comprising a sintered mixture of a metal and its metal oxide from the platinum group, the iridium group or gold.

18. A sensor in accordance with claim 17, wherein said stacked arrangement of electrodes includes a reference electrode comprising doped diamond or diamond-like carbon.

19. A sensor in accordance with claim 1, further comprising readable means for storing sensor-specific data.

20. A sensor in accordance with claim 19, wherein said readable means for storing sensor-specific data comprises at least one EEPROM or a transponder.

21. A sensor in accordance with claim 19, wherein said readable means for storing sensor-specific data are set up to store type information and/or information on the sensitivity of the sensor and/or on a performed gauging and/or calibration and/or information relevant for approval.

22. A sensor in accordance with claim 1, wherein said measuring electrode comprises a plurality of measuring electrode sectors separated from one another electrically and each comprising a different electrode material.

23. A sensor in accordance with claim 1, wherein said sensor housing has a gas inlet opening for the entry of the gas to be measured, which communicates with the environment of the sensor via a pneumatic damping element.

24. A sensor in accordance with claim 1, wherein said electrodes and/or a readable means for storing sensor-specific data are contacted via contact pins that can be inserted into said sensor housing and are in firm contact in the inserted state with said conductive connection means, which lead to said electrodes and/or said readable means for storing sensor-specific data and are electrically connected to these.

25. A sensor in accordance with claim 24, wherein said conductive connection means, which lead from the side of said contact pins that can be inserted into said sensor housing to said electrodes and/or to said readable means for storing sensor-specific data, comprise wires that lead at least partially through a liquid seal.

26. An electrochemical gas sensor, comprising:
a measuring electrode;
a counterelectrode;
a nonwoven layer, said measuring electrode and said counterelectrode cooperating with said nonwoven layer to form a stacked arrangement comprising said nonwoven layer arranged axially between said counterelectrode and said measuring electrode, said nonwoven layer being in contact with each of said counterelectrode and said measuring electrode and said nonwoven layer being in parallel with each of said counterelectrode and said measuring electrode, said nonwoven layer including a nonwoven layer extension extending radially outwardly from said stacked arrangement;
a porous membrane, that is permeable to air, in contact on at least one axial side with said stacked arrangement and arranged in parallel to said nonwoven layer, said counterelectrode and said measuring electrode, said porous membrane including a porous membrane extension extending radially outwardly from said stacked arrangement;

a housing defining a stacked arrangement volume with said stacked arrangement of electrodes therein and a radially outward separate equalization volume, said separate equalization volume being connected to said stacked arrangement volume via at least one opening through which pass only said nonwoven layer extension and said porous membrane extension, said separate equalization volume being located at least partially in a plane with said stacked arrangement and circumiferentially surrounding said stacked arrangement at least partially in said plane, said porous membrane being exposed by said housing, at least in partial areas, to ambient pressure; and electrolyte partially filling said separate equalization volume to provide electrolyte in said separate equalization volume and a remaining equalization space not filled with electrolyte.

27. A sensor in accordance with claim 26, wherein:

said equalization volume surrounds the electrode arrangement along a closed figure;

said stacked arrangement occupies essentially a circular area;

said at least one opening comprises a plurality of circumferentially distributed openings;

said porous membrane extension comprises porous membrane strips arranged in a spaced apart and circumiferentially distributed pattern and each of said porous membrane strips extending from an edge of said circular area through one of said openings and into said equalization volume, wherein the end of at least one of said porous membrane strips extends into said remaining equalization space not filled with electrolyte in said equalization volume; and said nonwoven layer extension comprises nonwoven layer strips arranged in a spaced apart and circumiferentially distributed pattern, each of said nonwoven layer strips extending from the edge of said circular area into said equalization volume, wherein the end of at least one of said nonwoven layer strips extends into the electrolyte in said equalization volume.

* * * * *